United States Patent
Kurth et al.

(10) Patent No.: US 6,966,896 B2
(45) Date of Patent: Nov. 22, 2005

(54) INTRODUCER AND HEMOSTATIC VALVE COMBINATION AND METHOD OF USING THE SAME

(75) Inventors: Paul Kurth, Rancho Palos Verdes, CA (US); Andrew William Armour, Media, PA (US); Sarah Ambryn Neilans, Gaithersburg, MD (US)

(73) Assignees: Paul A. Kurth, Santa Barbara, CA (US); Thomas Medical Products, Inc., Malvern, PA (US)

( * ) Notice: Subject to any disclaimer, the term of this patent is extended or adjusted under 35 U.S.C. 154(b) by 117 days.

(21) Appl. No.: 10/234,686

(22) Filed: Sep. 4, 2002

(65) Prior Publication Data

US 2004/0054330 A1    Mar. 18, 2004

(51) Int. Cl.[7] .............................................. A61M 5/178
(52) U.S. Cl. ........................... 604/167.06; 604/164.05; 604/160
(58) Field of Search ................................ 604/160, 161, 604/164.05, 164.07, 107.01, 167.03, 167.04, 604/256, 164.01, 167.06, 166.01, 169, 905, 604/158, 236, 702, 201, 200, 533, 247, 245; 251/368, 149.1

(56) References Cited

U.S. PATENT DOCUMENTS

| | | | | |
|---|---|---|---|---|
| 5,312,355 A | * | 5/1994 | Lee | 604/160 |
| 5,755,693 A | * | 5/1998 | Walker et al. | 604/160 |
| 6,159,198 A | * | 12/2000 | Gardeski et al. | 604/523 |
| 6,712,791 B2 | * | 3/2004 | Lui et al. | 604/167.04 |

* cited by examiner

*Primary Examiner*—Nicholas D. Lucchesi
*Assistant Examiner*—Matthew F DeSanto
(74) *Attorney, Agent, or Firm*—Daniel L. Dawes; Myers Dawes Andras & Sherman LLP

(57) ABSTRACT

An introducer and hemostatic valve for improved torsional guidance and kink resistance includes an entirely circumferentially reinforced introducer connected directly to a valve body formed of a plurality of separable portions and housing a valve element in a central chamber thereof. The plurality of portions may be attached to the introducer during formation of the introducer, the valve body, or both. Alternatively, the plurality of portions may be attached to the introducer by assembly of the portions together in a surrounding relation to the introducer. In use, the plurality of portions are separated from each other and the introducer is cut along its length in order to withdraw the introducer and hemostatic valve over an enlarged proximal end of an access device as the introducer is pulled from the patient's body.

14 Claims, 8 Drawing Sheets

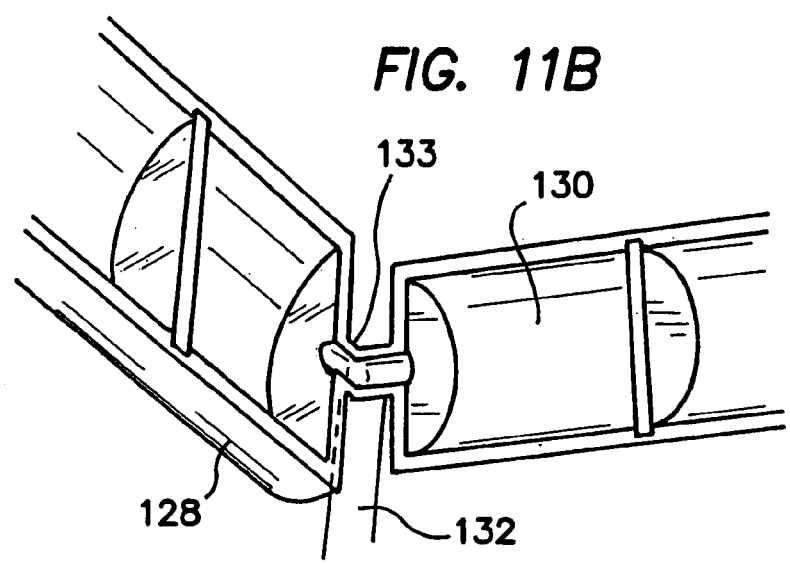
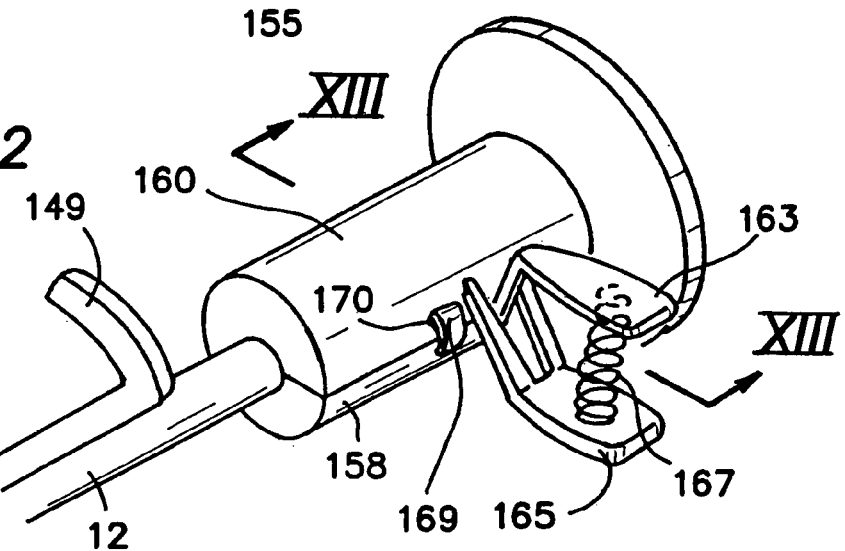
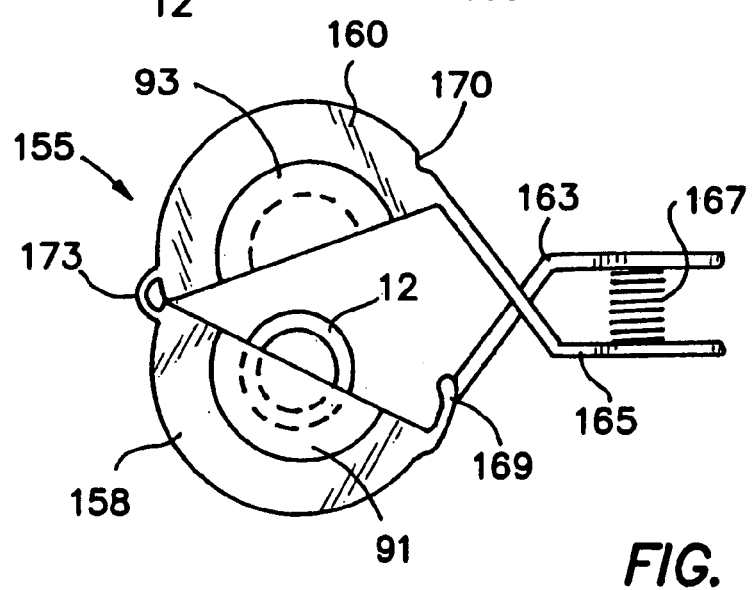

INTRODUCER AND HEMOSTATIC VALVE COMBINATION AND METHOD OF USING THE SAME

BACKGROUND OF THE INVENTION

1. Field of the Invention

The invention relates generally to introducers, sheaths, guides or catheters and hemostatic valves, and more specifically to a nonfrangible guide or introducer and hemostatic valve combination and the method of using the same.

2. Description of the Prior Art

For purposes of this specification a sheath is defined as an un-reinforced hollow tube, which may contain lines of weakness to aid in the peeling apart of the sheath.

A guide is a braid-reinforced hollow tube that cannot be peeled, or torn away simply by pulling on it, but must be sliced or cut open with a cutter, slicer, slitter or other tool. Further, while the guide is disclosed as braided, any construction of the guide, which allows the guide to be torsionally stiff enough such that a rotation of its proximal end is transmitted in its substantial entirety to its distal end when the guide is in use, is considered equivalent. Thus, the guide is termed, "nonfrangible".

A catheter is a general term used to describe a tube that may be braided or not, and is generally used to inject or aspirate fluids.

An introducer is a general term used to describe a sheath or guide that is used to introduce another medical device into the body.

The prior art has a variety of guides, introducers and catheters in combination with hemostatic valves, wherein the catheters or introducers are of the frangible type. Most of these prior art devices also require introducers that are of a stiffer material to aid in insertion of a catheter sheath into a patient's vein.

Of particular interest is U.S. Pat. No. 6,083,207 to Heck, which is incorporated herein by reference. Heck's device incorporates a frangible introducer. Morris, U.S. Pat. No. 5,713,867 is directed to a braided introducer having a pair of symmetrically opposed tabs on its proximal end, which introducer is slit by a cutting tool or is torn along a weakened line. The tabs remain permanently affixed to each longitudinal half of the introducer. Morris does not clearly describe or show how the cutting tool is used to cut through the hub or the structure, which forms the base structure which connects the tabs to the introducer. In fact, it is believed that Morris is inoperable to function as a splittable introducer due to the barrier presented by the hub to any cutting step.

The frangible sheaths of the prior art cannot torqued as required to steer the distal end of the sheaths, namely to be steered through the subclavian vein into the right atrium, through the right ventricle, and into the pulmonary artery. This and other steering requirements necessitate that the sheath be reinforced to transmit the torsional forces applied to its proximal end to its distal end during guiding.

The prior art is further deficient in that it lacks an adequate showing or disclosure relating to removable or openable hemostatic valves directly and integrally connected to a guide.

The prior devices are also lack hemostatic valve bodies having weakened lines along which the valve body may be broken into at least two portions, wherein one of the portions are integrally connected with the introducer and one separable to allow for cutting of the reinforced introducer.

While the prior art shows some hemostatic valve bodies that open on a hinge, the prior art fails to show such valve bodies directly connected to a guide.

BRIEF SUMMARY OF THE INVENTION

The invention overcomes these deficiencies with an introducer and hemostatic valve combination for improved steering or transmission of torsional forces that includes an introducer having a fully reinforced construction. The hemostatic valve has a body comprised of a plurality of separable portions, which form a central chamber. A valve membrane is disposed in the central chamber to provide a fluid-tight seal with or without any elongate instrument being disposed through the chamber. A means is provided for holding the plurality of portions of the valve body together and the introducer is connected to the valve body by a fluid-tight connection.

The introducer and valve are also embodied by an introducer comprised of at least two components including a tube and a reinforcement. The reinforcement generally comprises at least one filament. The filament extends completely circumferentially around the tube a plurality of times. A plurality of filaments can be crisscrossed and oriented diagonally with respect to a length of the introducer. These filaments cause the introducer to be both torqueable and nonfrangible, thereby necessitating the introducer to be longitudinally separated or opened by longitudinally cutting or slitting the introducer in order to remove it over an enlarged lead connection on a proximal end of the lead. The introducer is "torqueable" in that it resists rotational deformation when a rotational or torqueing force is applied to the introducer. Alternatively stated, the introducer is capable of transferring a torsional force applied at one end to the other end. It is also contemplated that any means now known or later devised other than that set forth above may provide "torqueability" and be deemed equivalent.

A variety of embodiments are expressly contemplated with regard to the introducer's connection to the valve body. The introducer may be removably connected to the valve body by assembling the plurality of portions of the valve body together with the introducer, e.g. using a mechanical compression fitting.

Alternatively, the plurality of portions of the valve body may be integrally molded together and have a weakened line along which the body may be selectively broken into separate portions. In this case, the separate portions of the valve body may be integrally connected to the introducer by insert molding and remain attached to the introducer even after being separated from each other.

Alternatively, a first portion of the valve body may be permanently attached to the introducer while a second portion of the valve body is removably attached to the first portion of the valve body or removably attached to the introducer.

Other embodiments include the case where a plurality of portions of the valve body are connected to each other on one side of the body by a hinge, and are separably and sealingly fastened to each other the opposing side of the valve body. In these embodiments, the portions of the valve body are formed of or comprise a resilient material such that the portions snap fit together.

In one embodiment of the above described hinged version of the invention, a resilient means for biasing the first portion and the second portion together is included. Furthermore, in this embodiment a first finger grip is connected to a first portion of the valve body and a second finger grip is connected to a second portion of the valve body for use in manually separating the first and second portions from each other against the bias of the resilient means.

In another embodiment of the invention, the plurality of portions of the valve body comprises a first portion and a second portion together forming a nipple for receiving the introducer.

In any of the above described embodiments, the plurality of portions of the valve body may comprise a first portion and a second portion that are substantially mirror images of each other. Alternatively, the first and second portions can merely be complementary to each other. In either case, the first and second portion forms a seal therebetween when assembled together.

The method of using the invention is determined by the details of the structure of the hemostatic valve, which includes a housing forming a central chamber and a plurality of separably interconnected portions. The method of using a reinforced introducer and hemostatic valve combination for improved torsional guidance of the introducer may also be utilized for introducing medical devices other than pacemaker electrical leads into vessels and cavities of a body. While the invention deals specifically with introducing a pacemaker electrical lead having a lead tip at a distal end and possibly an enlarged lead connection at a proximal end, the scope of the invention is broad enough to include any elongated instrument disposed through the introducer.

The method includes the steps of: inserting a needle into a vessel; inserting a guide wire in to the vessel; removing the needle by sliding it off of a proximal end of the guide wire; inserting a distal end of the reinforced introducer into the vessel with the hemostatic valve integrally attached to a proximal end of the introducer; effectively guiding the introducer by torsional manipulation to position the distal end of the introducer at a specific point of operation; removing the guide wire; inserting a pacemaker lead, tip first, through the introducer with the enlarged lead connection remaining at the proximal end of the pacemaker lead outside of the introducer; continuing to move a distal end of the pacemaker lead to the point of operation; separating the plurality of portions of the valve housing; and removing the introducer by cutting the introducer along its length so that the introducer can be removed over the enlarged lead connection while the pacemaker lead is left undisturbed at the point of operation.

It should be noted that the steps involving the needle and guide wire may be bypassed. These optional steps are often advantageously used to improve introduction and guidance of devices into a body.

The invention also includes a method of using a reinforced introducer and a hemostatic valve combination for improved torsional guidance of the introducer. As can be appreciated, the reinforced introducer can be guided when used by itself even without a guide wire because of the reinforcement. Once again, the method of using is applied to guiding an electrical lead having a lead connection on a proximal end and a lead tip at a distal end. However, the invention may be used to insert other devices into a vessel or cavity of the patient's body. As with all of the embodiments, the hemostatic valve has a housing comprising a plurality of separably connected portions forming a central chamber.

The method of using the invention includes the step of removing or withdrawing the valve housing and the reinforced introducer once the electrical lead has been properly located in a patient's body. When the valve housing has at least first and second portions, the step of removing may further comprise one or more of the following: detaching the second portion from the first portion and leaving the first portion attached to the introducer; separating the first and second portions from each other while leaving the first and second portions attached to the introducer; breaking the housing along at least one weakened line defining a boundary between the at least first and second portions; resiliently releasing a snap fitting between the first portion and the second portion; hingedly moving the first and second portions away from each other; and releasing the first portion and the second portion from each other by releasing a band or tape. It is to be understood that typically two tabs are connected to the valve body to assist in the manual separation of the valve body portions. In the invention one of the tabs remains connected at least to the introducer to allow the introducer to be held and accessed while it is then being cut or sliced with a tool.

The step of withdrawing the valve housing and the reinforced catheter introducer once the electrical lead has been properly located in a patient's body includes additional steps. In the device of the invention, the introducer comprises a nonfrangible introducer and requires the additional step of cutting the introducer. In this case, the step of withdrawing comprises separating at least a second portion from a first portion, holding the introducer by one of the portions and/or its associated tab, and cutting the nonfrangible, reinforced introducer along its length as the introducer is withdrawn from the patient's body and slid past the enlarged lead connection.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIGS. 11A, 11B and 11C are perspectives views of an embodiment in which the introducer is made integral with and remains attached to both portions of the valve housing.

FIG. 12 is a perspective view of an additional embodiment of the introducer and valve.

FIG. 13 is a modified sectional view taken along lines XIII—XIII of FIG. 12.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Figure 1:
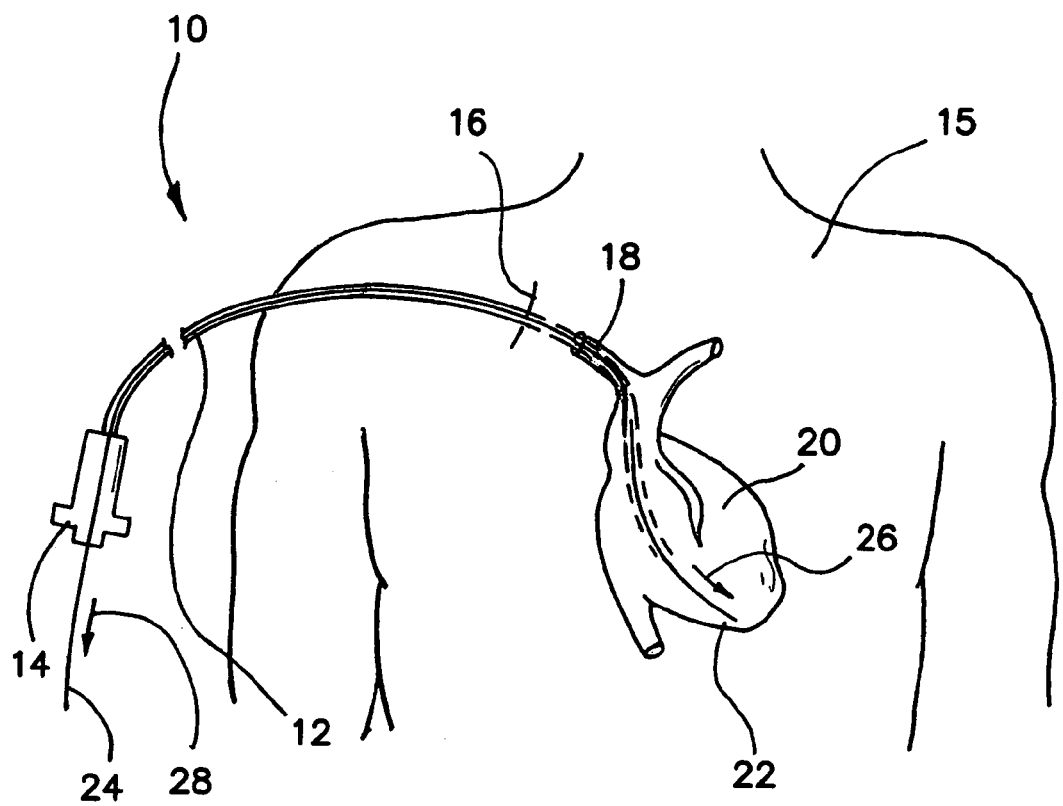
FIG. 1 is a diagrammatic view showing the introducer and hemostatic valve combination inserted through the subclavian vein and into the heart.

Consider first some background describing the context in which the illustrated embodiment is used. FIG. 1 depicts the introducer and valve combination 10 comprising the reinforced introducer 12 and hemostatic valve 14. As shown, the introducer 12 penetrates the patient 15 at the point of injection or insertion 16 and enters the subclavian vein 18. From thence, the introducer 12 is directed into the heart 20 and positioned to reach a point of implantation or operation 22.

As shown in FIG. 1, introducer 12 may be guided along previously inserted guide wire 24. The guide wire 24 is a known means for aiding in the guidance of catheters and in FIG. 1 guide wire 24 helps to guide introducer 12 in the direction of arrow 26 to point of operation 22. Once introducer 12 is in position, guide wire 24 may be withdrawn from introducer 12 and valve 14 in the direction of arrow 28. The guide wire 24 is optional in accessing point of operation 22. This is especially so in the invention because introducer 12 is reinforced to withstand torsional deformation. As such, introducer 12 can be provided with appropriate bends and can be manipulated to navigate its way to a point of operation as desired.

Figure 2:
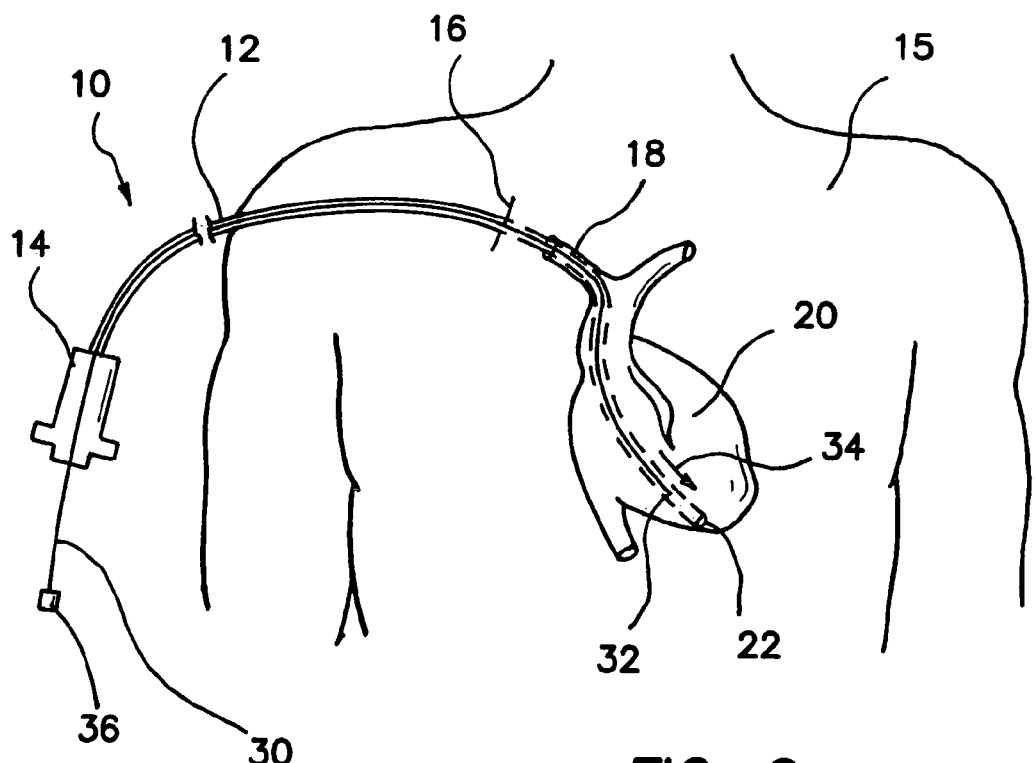
FIG. 2 is a diagrammatic view of the introducer and valve combination depicting the insertion of an electrical lead.

While the introducer and hemostatic valve 10 of the invention may be used for a variety of types of access to different parts of the body, of particular interest is the insertion of an electrical lead 30 for a pacemaker as shown in FIG. 2. Electrical lead 30 has a lead tip 32 at its distal end that is threaded or disposed through valve 14 and introducer 12 in a direction of arrow 34 toward the point of operation 22 in the heart 20. Electrical lead 30 has an electrical connector 36 at a proximal end thereof, which is of such a size and configuration that valve 14 and introducer 12 cannot be simply pulled over connector 36 off lead 30.

Figure 3:
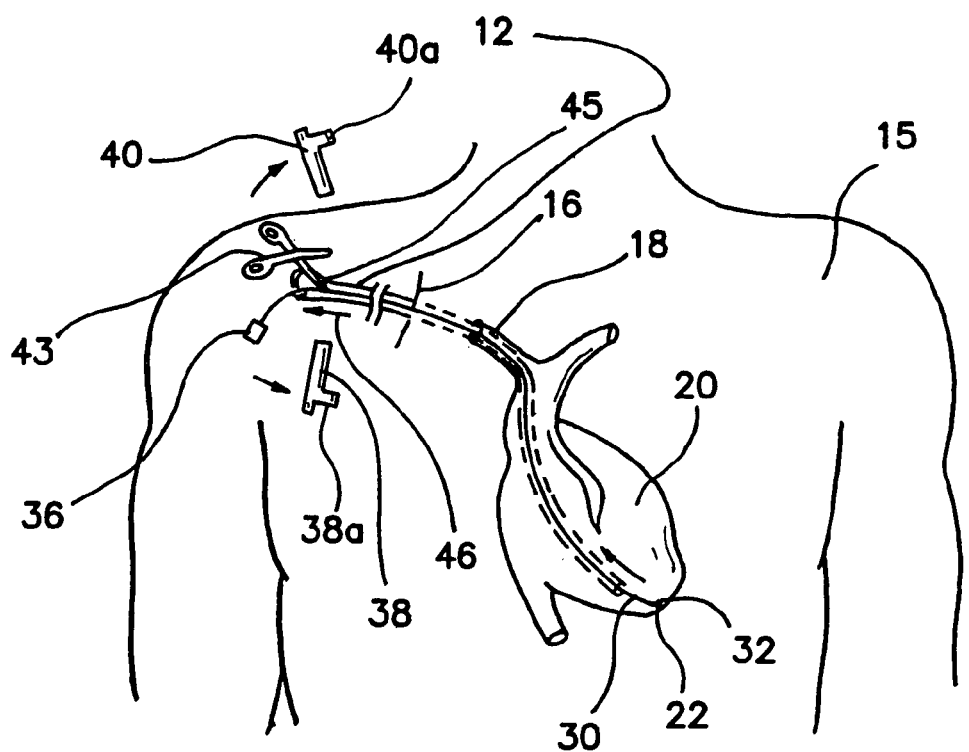
FIG. 3 is a diagrammatic view showing the removal of the valve and introducer.

As shown in FIG. 3, after the lead tip 32 has reached the point of operation 22, the introducer and valve combination 10 must be removed while the lead 30 remains in place. Valve 14 is made of at least a first portion 38 and a second portion 40, which include not only portions of the valve body surrounding, supporting and holding a valve membrane (not shown), but also include typically two opposing tabs 38a and 40a by which the portions 38 and 40 are held and manipulated. It is also expressly contemplated that at least one of the tabs 38a and 40a may be separable from remaining portions of the valve body and permanently attached to the introducer while the other tab is separable from the introducer with or separately from the removable valve body portions. The first and second portions 38, 40 can be separated at least enough to allow connector 36 to pass therebetween. The first and second portions 38, 40 are shown to completely separate from the introducer 12 in FIG. 3. However, in the preferred embodiments as discussed below, one of the first or second portions 38, 40 remains attached to the introducer 12 after relative separation.

The next step is to withdraw introducer 12. However, the electrical connector 36 is too large to pass through the inner diameter of introducer 12. Therefore introducer 12 is cut along its length by a slitter or cutting means 43. As introducer 12 is cut or slit, electrical lead 30 is permitted to slide through cut 45 and introducer 12 can be withdrawn from the heart and vein of the patient 15 in a direction of arrow 46 while the electrical lead is left inserted.

Figure 4:
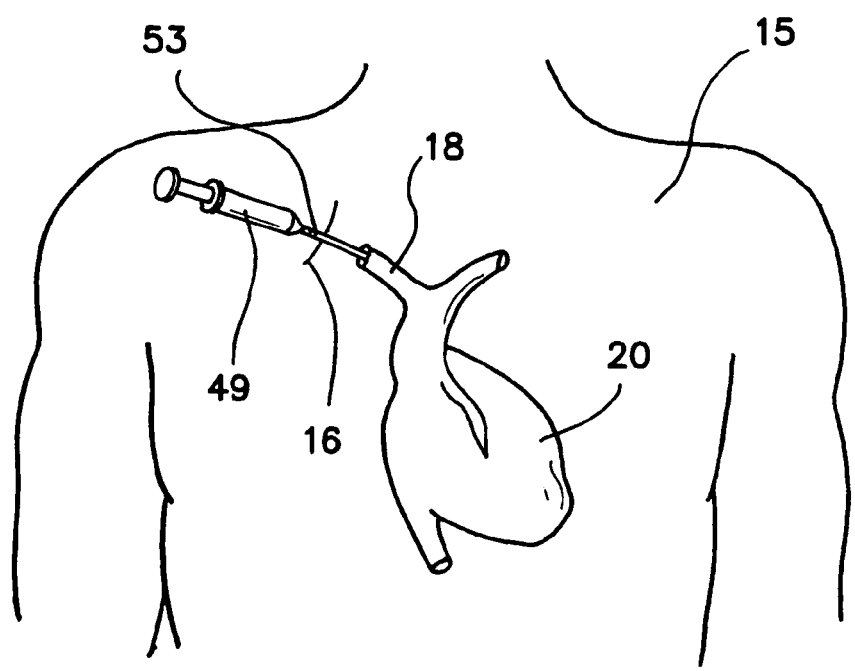
FIG. 4 is a diagrammatic view showing the preliminary step of inserting a needle into the subclavian vein.
Figure 5:
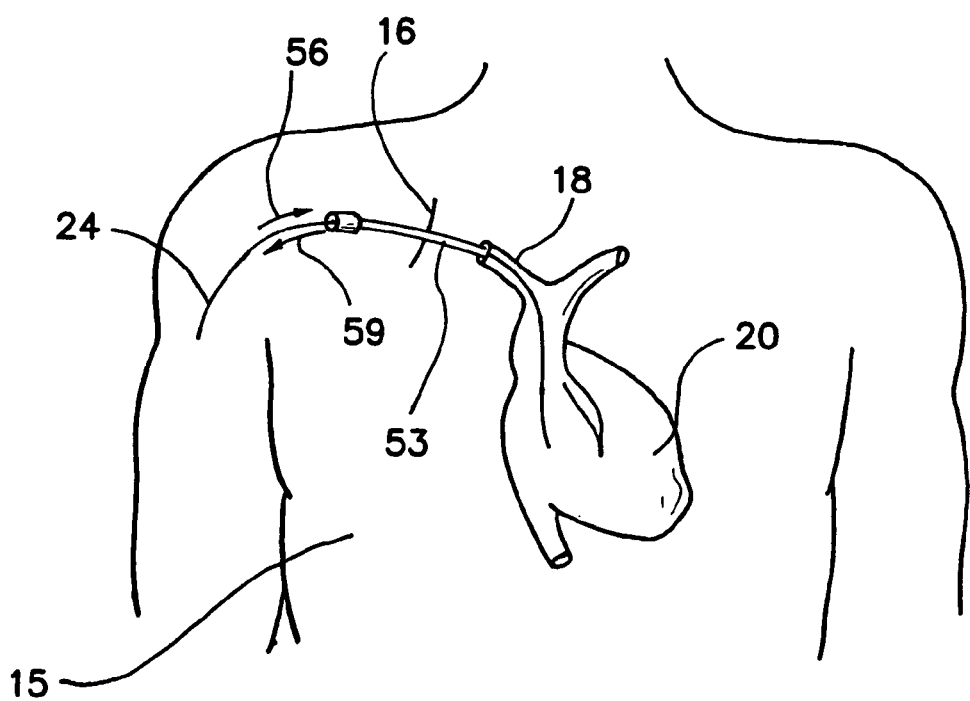
FIG. 5 is a diagrammatic view showing the preliminary step of inserting a guide wire and removing the needle shown in FIG. 4.

FIGS. 4 and 5 depict preliminary steps, which may be omitted or replaced by alternative means by which introducer 12 is permitted to penetrate into the subclavian vein 18. In FIG. 4 syringe 49 is used to insert a hypodermic needle 53 into the subclavian vein of the patient 15. The syringe 49 is then removed and a guide wire 24 is inserted through needle 53 in a direction of arrow 56 as shown in FIG. 5. Once guide wire 24 has been inserted, needle 53 may be withdrawn in a direction of arrow 59 and slid off of a proximal end of guide wire 24.

Figure 6:
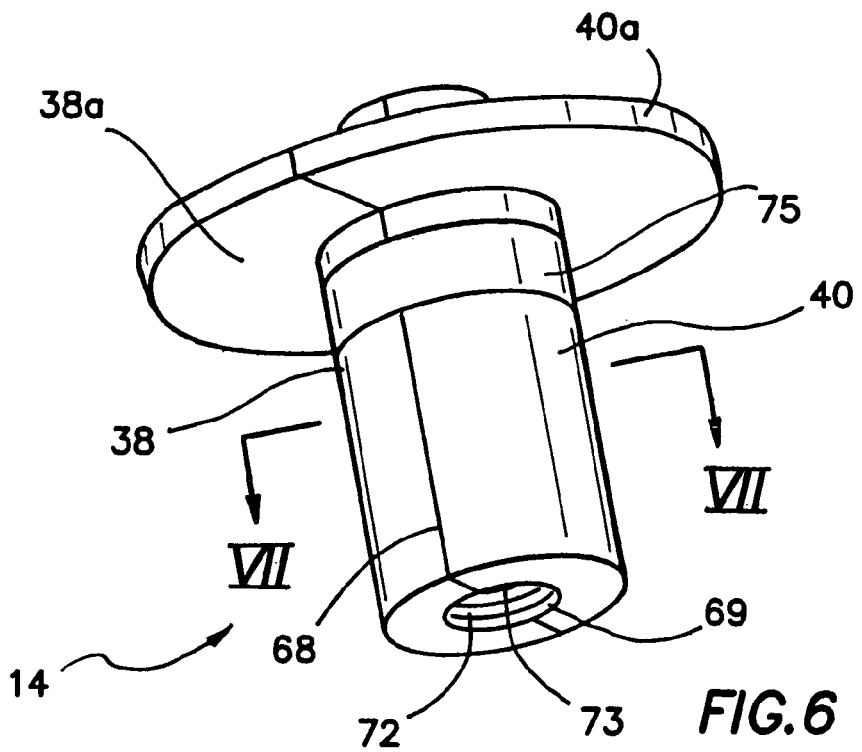
FIG. 6 is a perspective view of a hemostatic valve of the invention.

As shown in FIG. 6, the hemostatic valve 14 has a body comprising first and second portions 38, 40 and a tab 40a protruding outwardly from the portions 38, 40. First tab 38a extends from first the body portion 38, and a second tab 40a extends from second the portion 40. These tabs 38a, 40a are integral with the respective first and second portions 38, 40 and aid in separating portions 38, 40. The first and second portions 38, 40 are separated from each other by a seam, score line or weakened line 68. In some embodiments line 68 represents an actual physical discontinuity or break between first and second portions 38, 40 even when the portions are assembled together in use. In all cases, however, first and second portions 38, 40 define an aperture 69 at a distal end of valve 14. Associated with aperture 69 and located slightly interiorly thereof relative to body 14 is a sealing valve membrane 72 for providing a fluid tight seal with any lead disposed through valve 14.

As shown in FIG. 6, first and second portions 38, 40 of valve 14 form a central chamber 73 through which an electrical lead or other elongate instrument is passed during use. The first and second portions 38, 40 are depicted in FIG. 6 as being held together by tape or a band 75. However, as disclosed above by reference to weakened line 68, other means for holding first and second portions 38, 40 together may also be employed and are discussed below.

Figure 7:
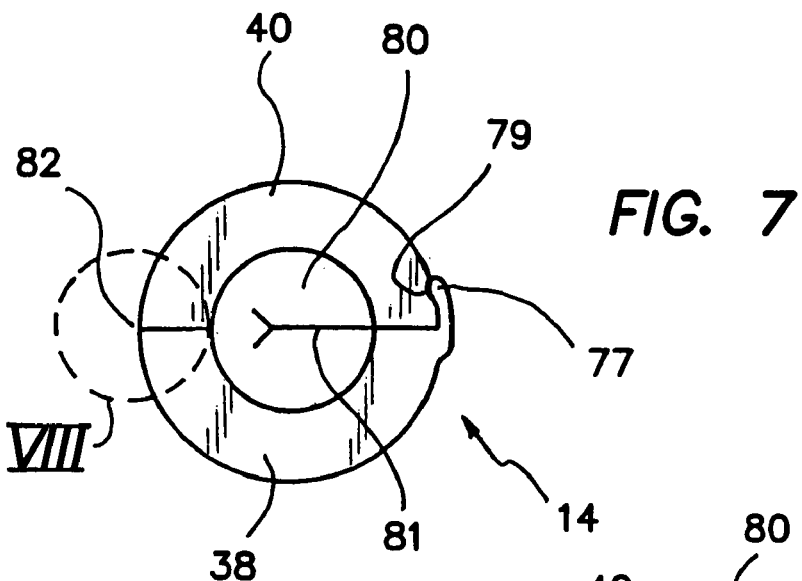
FIG. 7 is a sectional view taken along lines VII—VII of FIG. 6.

FIG. 7 is a cross-section taken along lines VII—VII of FIG. 6 and showing an alternative means of attachment including a tongue 77 and groove 79 serving as a latch or clasp. Also clearly shown in FIG. 7 is valve membrane 80 that substantially prevents blood from escaping during use of the invention. Valve membrane 80 prevents blood from escaping by means of a slit 81 defined in a soft, resilient polymer plug or cylinder, which comprises the body of membrane 80 and which slit in this case is in the form a "Y". The slit may of course have other shapes such as simple straight lines completely or partially extending across membrane 80, or "X" shapes and the like. As can be appreciated, opposite sides of valve membrane 80 press against each other at slit 81 and thereby form a seal. The attachment means 82 diametrically opposed to tongue 77 and groove 79 may be any of a variety of means to be described hereafter.

Figure 8A:
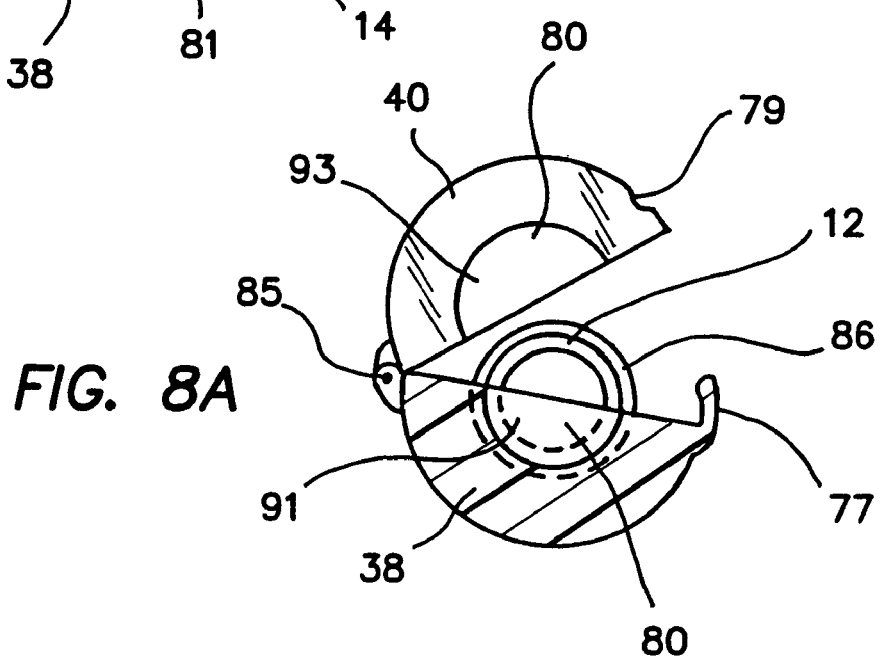
FIGS. 8A and 8B are sectional views similar to FIG. 7 and showing variations of the connection in the region indicated at VIII of FIG. 7.

One alternative attachment means 82 for region VIII of FIG. 7, is a hinge 85 as shown in FIG. 8A. In this way, the first and second valve portions 38, 40 may be rotated together to clamp around an annular protrusion 86 of introducer 12 to form a fluid-tight seal, and be locked in place by tongue and groove 77, 79. In this embodiment, valve membrane 80 is provided in two separate portions 91, 93, which are cut away for convenience in the view of FIG. 8A.

Figure 8B:
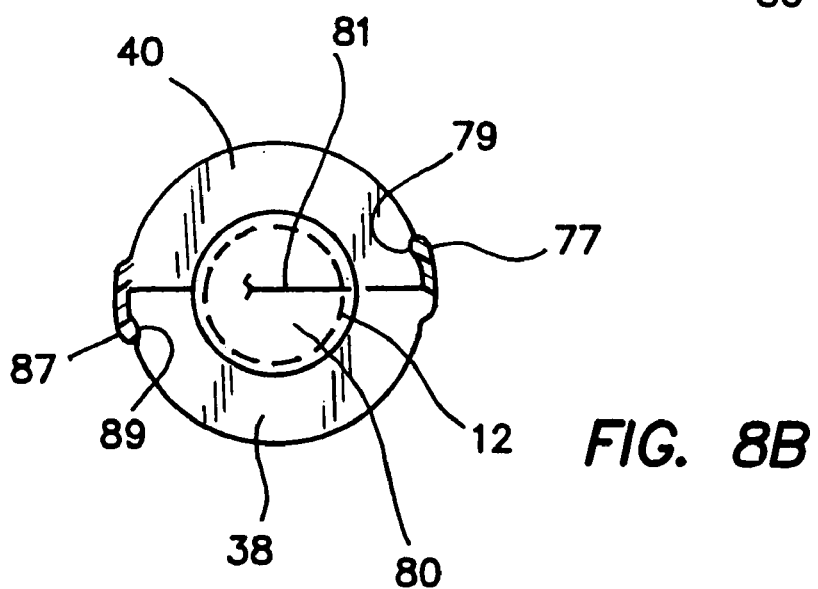

FIG. 8B shows a second alternative attachment means 82 for region VIII of FIG. 7 in the form of a second tongue 87 and groove 89 combination. FIG. 8B also shows that slit 81 may be of any length and may be simple or branchless. In each of the embodiments employing tongues and grooves, a resilient or elastomeric material is needed to provide the snap fit characteristics for locking the first and second portions 38, 40 together. As shown in FIGS. 8A and 8B, one or both of the portions may be formed of a resilient material, or the tongue 77 may be formed of a resilient material.

Figure 9:
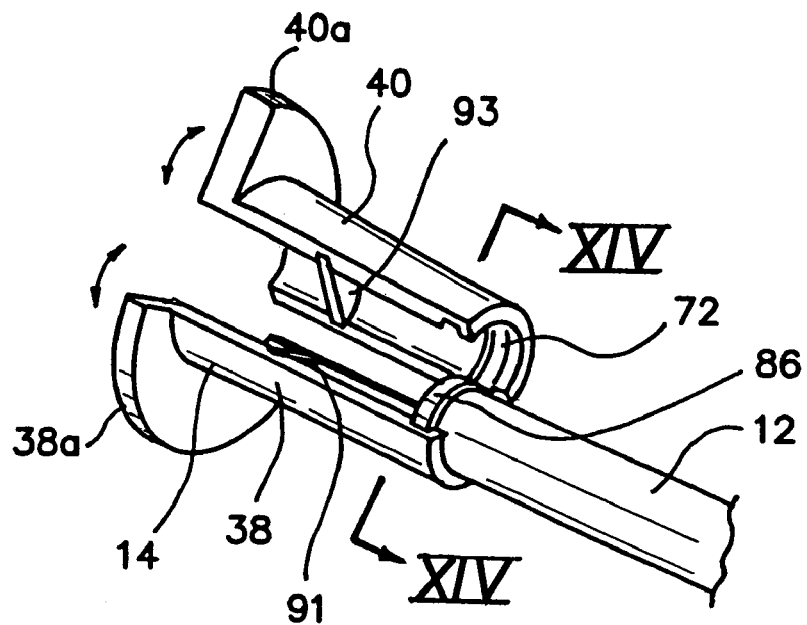
FIGS. 9 and 10 are perspective views of embodiments in which the introducer remains attached to one portion of the valve housing.

FIG. 9 shows the embodiment of FIG. 6 in which the first and second portions 38, 40 separate completely from each other and one of the portions 38, 40 separates from the introducer 12 while the other remains attached thereto. Preferably, the first portion 38 is permanently connected to the introducer 12. As such, the first portion 38 can function as a handle by which the surgeon holds onto introducer 12 during cutting of introducer 12 by a cutting means 43. In accordance with the completely separable portions of this embodiment, the valve comprises a first valve membrane 91 and a second valve membrane 93 each held integrally in respective first and second portions 38, 40.

Figure 10:
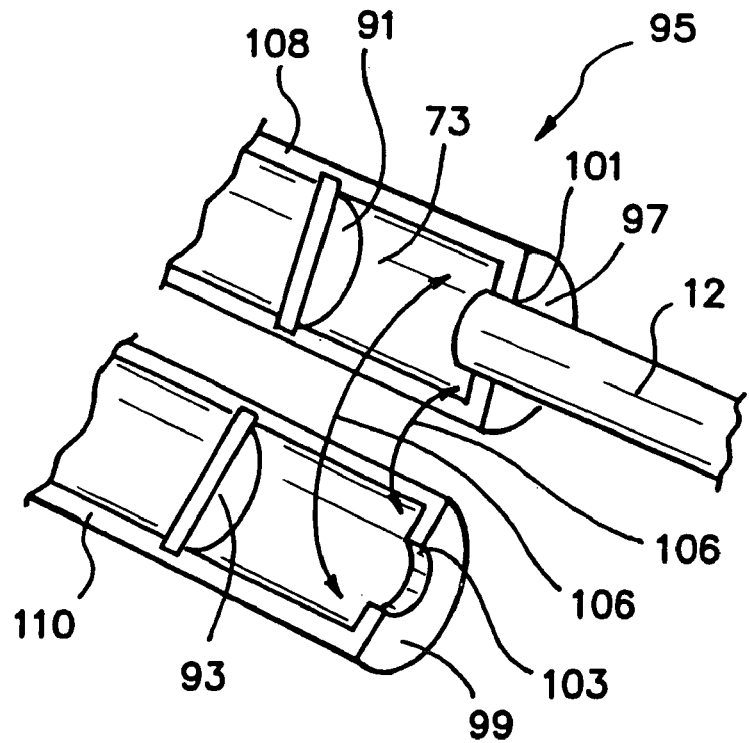

FIG. 10 shows an alternative embodiment 95 having a first valve portion 108 and a second valve portion 110. In this embodiment, introducer 12 is permanently attached to first portion 108 by insert molding or adhesion to a first aperture sector 101 in a first end wall 97. On the other hand, introducer 12 is removably and sealingly coupled to second portion 110 at a second aperture sector 103 in a second end wall 99 when the first and second portions 108, 110 are assembled together. A release agent can be applied to introducer 12 and/or sector 103 during manufacture so that when introducer 12 is insert molded to portions 108 and 110, no bond or a weakened bond is formed between introducer 12 and portion 110. Arrows 106 indicate directions of opening and closing the first and second portions 108, 110 relative to each other.

A preferred embodiment is comprised of a valve housing 38, 40, in the example of FIG. 9, connected to the guide 12 with a fluid tight connection that permits the transmission of torque from the valve housing 38, 40, to the guide 12. Upon separation of the valve housing 12, one portion, 38 for example, remains permanently attached to the guide 12 while the other portion 40 releasably separates from the guide 12 and the opposing valve portion 38 to expose the end of the guide 12 that is to be slit.

This is accomplished by the application of a release material onto the guide 12 prior to bonding the valve housing 38, 40 to the guide 12 either by insert molding (overmolding) or adhesive bonding. There are many suitable commercially available bonding release materials such as Silicone (MDX4-4159 manufactured by Dow Corning), Teflon, Lecithin, and Zinc Stearate. The release material is applied to the outer surface of the guide 12 as a coating, film, tape or extruded tube. It is applied only to the portion of the guide 12 that will be connected to the valve portion 40 that is to separate. This is performed with mechanical fixturing that allows alignment of the release material to the proximal portion of the guide 12 and subsequent alignment during insert molding or bonding to the valve housing 38.

Figure 11A:
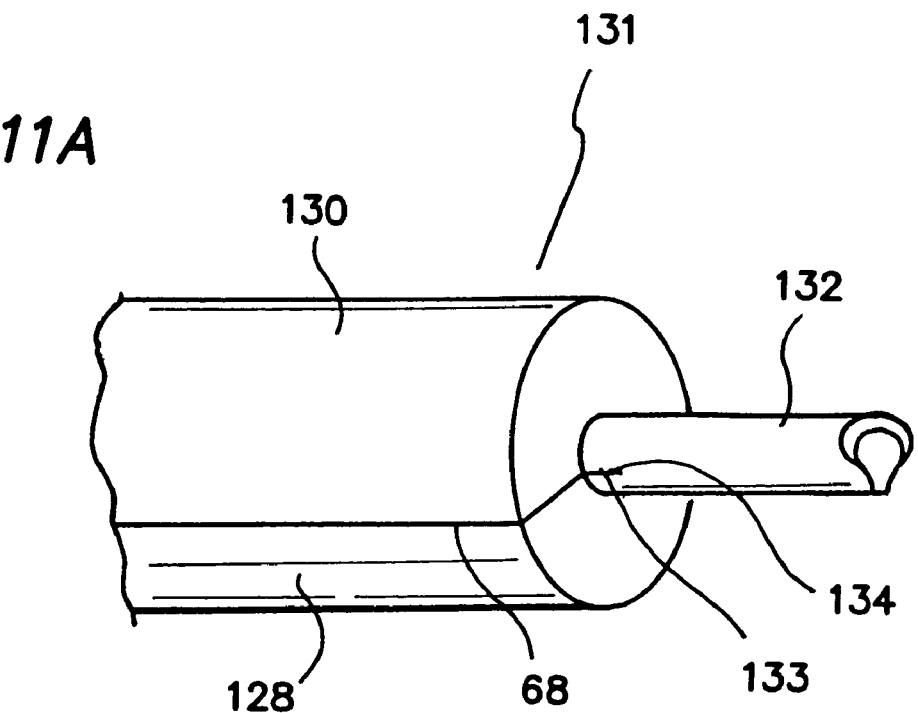

FIG. 11A shows an embodiment having an introducer 132 integrally formed with the hemostatic valve 131 comprising a first portion 128 and a second portion 130. In this embodiment, weakened line 68 runs into or is continuous with a line 133 on introducer 132. Weakened line 133 on introducer 132 ends in a stop 134 that prevents further tearing along the length of introducer 132. Stop 134 may be comprised of the beginning of the reinforcing braid in or on introducer 132. Thus, there is a short proximal section of introducer 132 next to valve 131 running the length of line 133 which is free of reinforcement. The shortness of this section allows its inclusion in introducer 132, because the amount of torsional deformation is limited by its short length and can be tolerated.

FIG. 11B shows the embodiment of FIG. 11A with first and second portions 128, 130 separated from each other, yet still integrally connected to the introducer 132. As can be appreciated, the integral configuration of the embodiment of FIGS. 11A and 11B may be achieved by a molding process and has the advantage of forming the combination of introducer 132 and valve 128, 130 in a single step. It can also be appreciated from FIG. 11A that without the separation or opening allowed by line 133 no part of the proximal portion of introducer 132 would effectively be exposed or accessible to a cutting or slitting tool. The separation of line 113 on one or both sides of the proximal portion of introducer 132 as shown in FIG. 11A allows a cutting tool to be inserted on a prestarted or beginning a slit or cut down the longitudinal length of introducer 132.

Figure 11C:
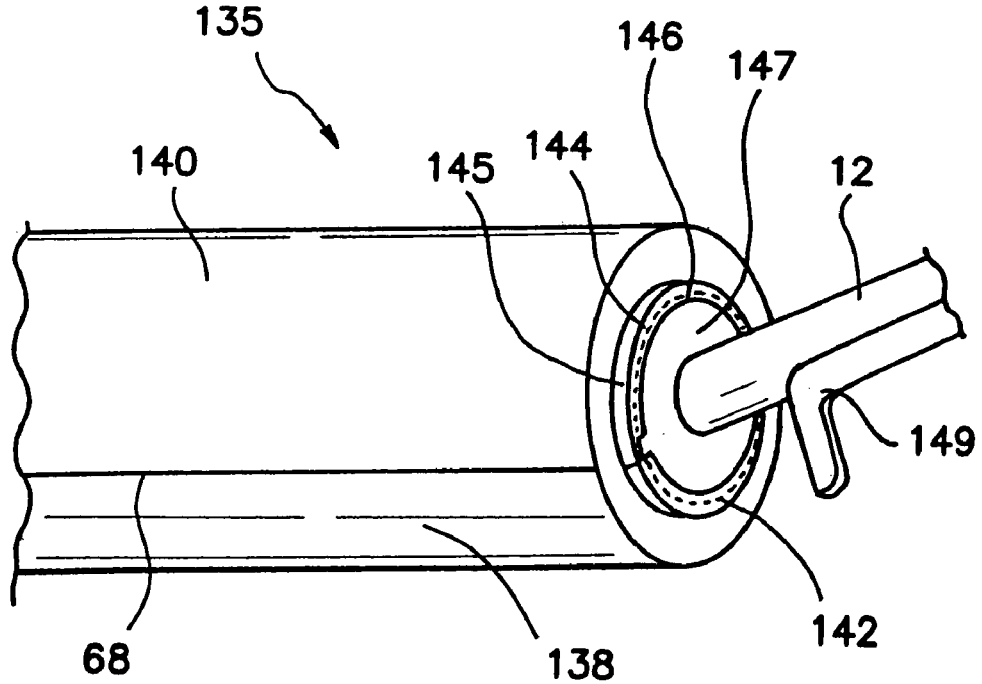

FIG. 11C shows an embodiment of a valve 135 similar to the embodiment of FIGS. 11A and 11B in that first and second portions 138, 140 may remain integrally attached to introducer 12 after separation from each other. A first seal retainer 142 on first portion 138 and a second seal retainer 144 on second portion 140 complement each other and provide a seal retainer 145 having an opening 146 for receiving reinforced introducer 12 in spaced relationship to valve 135. This space between valve 135 and the reinforced introducer 12 is for receiving a molded seal 147 that sealingly and integrally connects reinforced introducer 12 to the valve 135. Molded seal 147 may be reduced in size to be little more than a thin reinforcing ring of plastic or may be omitted all together in the case where reinforced introducer 12 is rigid enough to be insert molded to seal retainer 145. In this case a separate tab 149 is permanently affixed to one side of reinforced introducer 12, so that when both portions 138 and 140 of valve 135 are removed, reinforced introducer 12 can be held and restrained as a cutting tool is used to slit it open.

FIGS. 12 and 13 show a further additional alternative embodiment 155 of the hemostatic valve that includes a first portion 158 and a second portion 160. A first finger grip 163 is integrally connected to the first portion 158. A second finger grip 165 is integrally connected to the second portion 160. A biasing means in the form of a spring 167 urges the finger grips 163, 165 apart. Spring 167 also urges the first and second portions 158, 160 together by virtue of the crossed configuration of the finger grips 163, 165. This embodiment includes a tongue 169 and groove 170 for locking the first and second portions 158, 160 in a closed, sealed condition integral with the introducer 12 relative to the ambient when in use. Here again a tab 149 permanently affixed to introducer 12 is provided.

FIG. 13 is a modified sectional view taken along lines XIII—XIII of FIG. 12. FIG. 13 shows the hemostatic valve 155 in an opening configuration. Like the various embodiments described above, the introducer 12 may be temporarily attached to one or both of the first and second portions 158, 160. However, this particular embodiment is made functional by the hinge connection on one side of the valve 155, which is in the form of the flexible web-type hinge 173 in the embodiment shown.

It is to be expressly understood that in all of the embodiments, the portion or portion of the valve body or separately provided tab that remains attached to the introducer is functional as a handle to hold and manipulate the introducer during steps after the insertion of the electrical lead or other accession device. Such a handle is especially important during steps of cutting or slitting the introducer and withdrawal thereof.

Figure 14A:
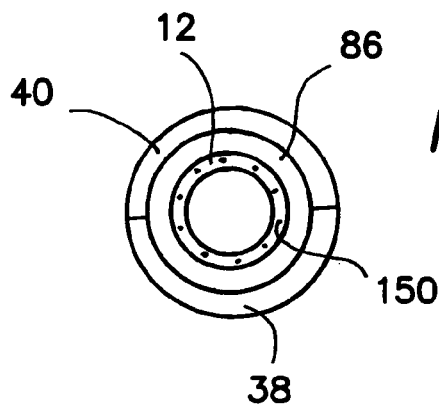
FIG. 14A is a sectional view taken along lines XIV—XIV of FIG. 9.
Figure 14B:
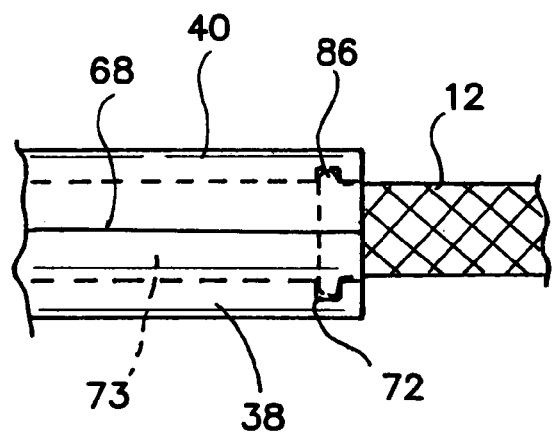
FIG. 14B is a partial side elevation view of the introducer and valve embodiment of FIG. 9.

FIG. 14A is a section taken along lines XIV—XIV of FIG. 9. However, the reinforcement details of the introducer apply to all the introducer embodiments of the invention. That is, the introducer 12, 132 is a non-frangible introducer along a major portion of its length by virtue of reinforcement filaments 150. The reinforcement filaments 150 may be on an outside, an inside, or may be embedded in the introducer 12, 132. The reinforcement of the introducer 12, 132 provides resistance against torsional deformation of the introducer. As such, the reinforced introducer 12, 132 can be better guided through vessels and through the heart. However, unlike the frangible sheaths of the prior art, the introducer 12, 132 of the invention requires slicing the wall and the reinforcement elements 150 of the introducer 12, 132 in order to move the introducer past an enlarged proximal end of an access device. FIG. 14B is a side elevation view. In FIGS. 14A and 14B, the annular protrusion 86 is shown seated in the sealing means 72, which in this case takes the form of a groove. The annular protrusion 86 may be formed integrally with the introducer 12, 132 or may be added to the introducer. In either case, the material of annular ring 86 must have properties that enable it to be cut once the first and second portions 38, 40 have been separated from each other.

However, it is to be understood that in the preferred embodiment when insert molding onto a bondable tube, there is typically no flare or tab. Adherence is obtained by a thermal bond between the plastic and the outer surface of the guide. A flare or tab would be used when connecting to materials which resist bond formation like Teflon®.

Figure 14C:
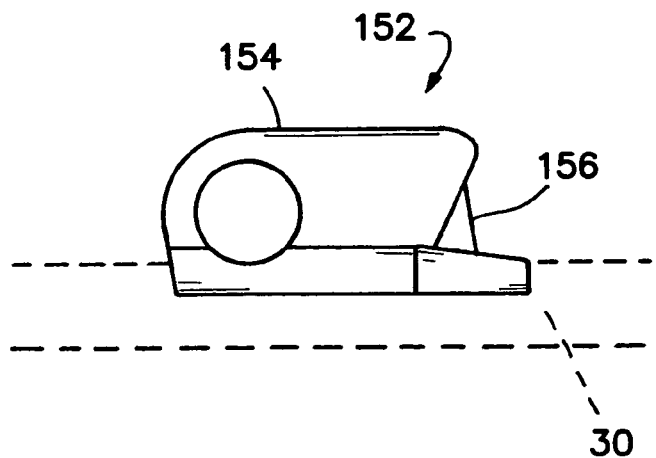
FIG. 14C is a side elevation view of an introducer slitter.
Figure 14D:
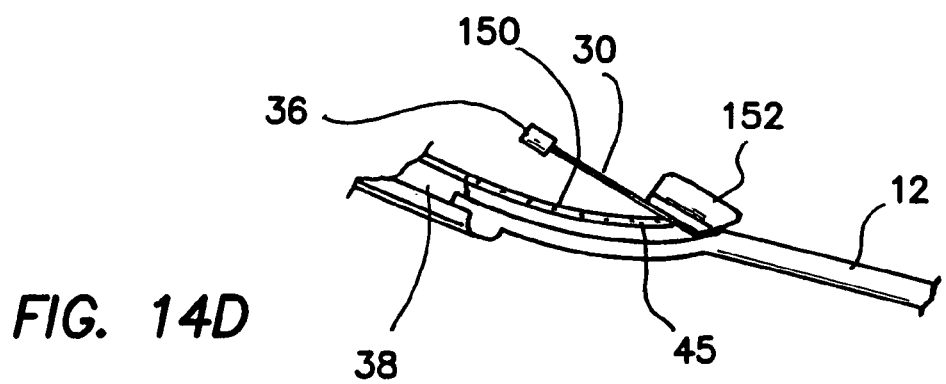
FIG. 14D is a perspective view of the introducer slitter cutting an introducer.

FIG. 14C shows a cutting means in the form of a slitter 152 having a grip portion 154 and a blade 156. FIG. 14D shows the slitter 152 in action forming cut 45 along the length of the introducer 12.

While a variety of embodiments have been set forth, the preferred embodiment includes the score line or weakened line 68 for breaking or cracking open the valve body. Furthermore, preferably the introducer is integrally connected to at least one of the valve body portions. The integral connection of the valve body to the introducer is particularly advantageous when at least one of the portions and the introducer can be molded together in a single molding operation. It further follows that integrally molding all of the portions together is also advantageous.

The scope of the invention expressly includes the adherence of a portion of the valve body or hub to the guide or sheath and a portion of the valve body or hub to be easily removed, so that the valve body or hub need not be cut through in order to cut the guide or sheath. Direct access of the cutting tool to the guide or sheath is afforded and a means is still providing for conveniently holding on to the guide or sheath to restrain it in place during cutting and/or to draw it over the cutting tool. A release coating or film is disposed onto the portion of the guide or sheath where the valve body or hub is to release. During bonding of the valve body or hub to the guide, the guide or sheath is keyed so that the appropriate portion of the guide or sheath, namely the portion with the release coating, is positioned in the correct orientation relative to the portion of the valve body or hub that is to separate from the guide or sheath. The valve body or hub may be bonded with adhesive, by insert molding or any other means now known or later devised in the art. The physical properties of the coating allow a fluid tight seal, and still allow a portion of the valve body or hub to be easily removed exposing the end of the guide or sheath for subsequent cutting.

The valve may be any type hemostatic valve now know or later devised. While various type of splittable valves have been described above, the invention expressly contemplates being used as an adapter for translatable or slideable valves which are moved or rotated into and out of an operative position, such as shown in U.S. Pat. No. 5,441,504 or PCT Publication WO 02/05867, both of which are incorporated herein by reference.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An apparatus in combination with an elongate instrument comprising:
    an introducer having a proximal end,
    a separable hemostatic valve coupled to the proximal end of the introducer,
    wherein only one portion of the hemostatic valve remains permanently connected to the proximal end of the introducer as a means for manually holding the introducer in position when the separable hemostatic valve is separated into at least two portions, the remaining portion of the proximal end of the introducer, which is not coupled to the one portion of the hemostatic valve, then being free of all obstructions which could interfere with separation of the introducer along a longitudinal axis of the introducer; and
    wherein the introducer has at least two components including a tube and a reinforcement rendering the introducer nonfrangible, and necessitating the cutting of the introducer longitudinally in order to permit removal of the introducer from the elongate instrument disposed therethrough without requiring the sheath and hemostatic valve to be removed from an end of elongate instrument.

2. The apparatus of claim 1, wherein the hemostatic valve comprises a separable valve body and wherein the separable valve body comprises a plurality of portions and the plurality of portions of the valve body comprise a first portion and a second portion connected to each other on a side of the body by means of a hinge, in which the first portion and the second portion are separably, and sealingly fastened to each other on an opposing side of the body.

3. The apparatus of claim 2, further comprising: a resilient means for biasing the first portion and the second portion together; and a first finger grip connected to the first portion and a second finger grip connected to the second portion for manipulating in order to separate the first portion and the second portion from each other.

4. The apparatus of claim 2, wherein: the separable valve body comprises a plurality of portions; and the introducer is connected to the valve body by assembling the plurality of portions together with a compression fit.

5. The apparatus of claim 1, wherein the hemostatic valve comprises a separable valve body and wherein the separable valve body comprises a plurality of portions; and the plurality of portions are integrally molded together and have a weakened line along which the body may be selectively broken in to separate ones of the plurality of portions.

6. The apparatus of claim 5, wherein the introducer is connected to the valve body by assembling the plurality of portions together in a compression fit.

7. The apparatus of claim 1 in combination with an elongate instrument having an enlarged portion on a proximal end, wherein the introducer has at least two components including a tube and a reinforcement, the reinforcement having at least one filament extending completely circumferentially a plurality of times about the tube thereby rendering the introducer nonfrangible, and necessitating the cutting of the introducer longitudinally in order to pass the introducer over the enlarged portion when the instrument has been inserted through the introducer.

8. The apparatus of claim 1, wherein the hemostatic valve comprises a separable valve body and wherein: the separable valve body comprises a plurality of portions; and the introducer is connected to the valve body by assembling the plurality of portions together with a compression fit.

9. The apparatus of claim 1, wherein the hemostatic valve comprises a separable valve body and wherein: the separable valve body comprises a plurality of portions; and the plurality of portions of the valve body comprises a first portion and a second portion formed of a resilient material such that the portions snap fit together.

10. The apparatus of claim 1, wherein the hemostatic valve comprises a separable valve body formed as one portion and comprising a plurality of parts, said parts being integrally formed together with the introducer as a unitary element.

11. The apparatus of claim 1, wherein the hemostatic valve comprises a separable valve body and wherein:
    the separable valve body comprises a plurality of portions;
    the plurality of portions of the valve body comprise a first portion and a second portion; and
    the first and second portions are substantial mirror images of each other.

12. The apparatus of claim 1, wherein the hemostatic valve comprises a separable valve body and wherein: the separable valve body comprises a plurality of portions; the plurality of portions of the valve body comprise a first portion and a second portion; and the first and second portions are complementary to each other.

13. The apparatus of claim 1 further comprising a cutting means having a grip portion and a blade to cut along the longitudinal length of the introducer as the introducer is drawn over the blade by pulling the introducer by the connected part of the valve body or tab.

14. A valved introducer assembly in combination with an elongate instrument comprising:
    an introducer having a longitudinal axis, a proximal end and a tubular body;
    an hemostatic valve assembly openable into two portions coupled to proximal end of the introducer,
    wherein only one portion of the hemostatic valve assembly remains permanently connected to the proximal end of the introducer as a means for holding the introducer in position when the openable hemostatic valve assembly is opened, wherein a portion of the proximal end of the tubular body of the introducer is free of all obstructions which could interfere with separation of the introducer along a longitudinal axis of the introducer while the remaining portion of the proximal end of the introducer remains securely connected to the one portion of the hemostatic valve assembly; and
    wherein the introducer has at least two components including a tube and a reinforcement rendering the introducer nonfrangible, and necessitating the cutting of the introducer longitudinally in order to permit removal of the introducer from the elongate instrument disposed therethrough without requiring the sheath and hemostatic valve to be removed from an end of elongate instrument.

* * * * *

UNITED STATES PATENT AND TRADEMARK OFFICE
CERTIFICATE OF CORRECTION

PATENT NO. : 6,966,896 B2
APPLICATION NO. : 10/234686
DATED : November 22, 2005
INVENTOR(S) : Paul Kurth et al.

It is certified that error appears in the above-identified patent and that said Letters Patent is hereby corrected as shown below:

Replace the term "sheath" found in claim 1, column 11, line 30, with the term "tube."

Replace the term "sheath" found in claim 14, column 12, line 62, with the term "tube."

Signed and Sealed this

Twenty-seventh Day of July, 2010

David J. Kappos
*Director of the United States Patent and Trademark Office*